United States Patent
Li et al.

(10) Patent No.: US 11,293,889 B2
(45) Date of Patent: Apr. 5, 2022

(54) FLUID ANALYZER FOR MEASURING A TARGET ANALYTE AND METHOD OF CALIBRATING AN AMPEROMETRIC SENSOR

(71) Applicant: Siemens Healthcare Diagnostics Inc., Tarrytown, NY (US)

(72) Inventors: Jay Li, Franklin, MA (US); Andy Chan, Franklin, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 569 days.

(21) Appl. No.: 16/310,079

(22) PCT Filed: Jun. 6, 2017

(86) PCT No.: PCT/US2017/036059
§ 371 (c)(1),
(2) Date: Dec. 14, 2018

(87) PCT Pub. No.: WO2017/218231
PCT Pub. Date: Dec. 21, 2017

(65) Prior Publication Data
US 2019/0128832 A1 May 2, 2019

Related U.S. Application Data

(60) Provisional application No. 62/356,632, filed on Jun. 30, 2016, provisional application No. 62/351,377, filed on Jun. 17, 2016.

(51) Int. Cl.
*G01N 27/327* (2006.01)
*G01N 27/404* (2006.01)
(Continued)

(52) U.S. Cl.
CPC ....... *G01N 27/3274* (2013.01); *G01N 27/404* (2013.01); *G01N 27/4163* (2013.01); *G01N 33/4925* (2013.01); *G01N 33/48707* (2013.01)

(58) Field of Classification Search
CPC .......... G01N 27/3274; G01N 33/4925; G01N 27/4163; G01N 27/404; G01N 33/48707
See application file for complete search history.

(56) References Cited

U.S. PATENT DOCUMENTS

| | | |
|---|---|---|
| 4,571,292 A | 2/1986 | Liu et al. |
| 5,185,263 A | 2/1993 | Kroneis et al. |

(Continued)

OTHER PUBLICATIONS

Canadian Office Action of Application No. 3,027,849 dated Dec. 6, 2019.

(Continued)

*Primary Examiner* — Joshua L Allen
(74) *Attorney, Agent, or Firm* — Dunlap Codding, P.C.

(57) ABSTRACT

A control system for a fluid analyzer is described. The control system has a processor executing processor executable code to: control a potentiostat to apply a first voltage potential sufficient to induce a first electrochemical reaction of a target analyte or a reaction byproduct of the target analyte in a sample of the calibration reagent and receive a first reading from the potentiostat; control the potentiostat to apply a second voltage potential insufficient to induce a second electrochemical reaction of the target analyte or a reaction byproduct of the target analyte in the sample of the calibration reagent and receive a second reading from the potentiostat; calculate calibration parameters using the first reading, the second reading and a multi-point calibration algorithm; and measure a target analyte concentration within the fluid sample using the calibration parameters.

11 Claims, 6 Drawing Sheets

(51) Int. Cl.
*G01N 27/416* (2006.01)
*G01N 33/49* (2006.01)
*G01N 33/487* (2006.01)

(56) References Cited

U.S. PATENT DOCUMENTS

| | | | |
|---|---|---|---|
| 5,376,244 A * | 12/1994 | Preidel | C12Q 1/001 |
| | | | 205/786 |
| 5,387,329 A * | 2/1995 | Foos | C08F 220/14 |
| | | | 204/403.06 |
| 5,550,053 A | 8/1996 | Salpeter | |
| 5,562,815 A * | 10/1996 | Preidel | G01N 27/404 |
| | | | 204/400 |
| 5,710,371 A * | 1/1998 | Czernecki | G01N 27/4163 |
| | | | 204/421 |
| 6,066,249 A | 5/2000 | Manzoni et al. | |
| 6,438,501 B1 | 8/2002 | Szecsody et al. | |
| 8,000,918 B2 | 8/2011 | Fjield et al. | |
| 8,211,292 B2 | 7/2012 | Brown | |
| 8,518,237 B2 | 8/2013 | Chan et al. | |
| 2003/0057108 A1 * | 3/2003 | Sridharan | A61B 5/14539 |
| | | | 205/775 |
| 2004/0137633 A1 * | 7/2004 | Shin | G01N 27/3274 |
| | | | 204/400 |
| 2006/0219575 A1 | 10/2006 | Oberlin | |
| 2009/0119047 A1 * | 5/2009 | Zelin | G01N 27/3274 |
| | | | 702/82 |
| 2011/0180426 A1 * | 7/2011 | Chan | G01N 27/404 |
| | | | 205/782.5 |
| 2015/0101938 A1 | 4/2015 | Bychkova et al. | |
| 2016/0186229 A1 * | 6/2016 | Hall | G01N 27/3274 |
| | | | 435/14 |
| 2017/0219515 A1 * | 8/2017 | Davis | G01N 27/404 |
| 2018/0246055 A1 * | 8/2018 | Naidu | G06N 3/086 |

OTHER PUBLICATIONS

Slejko et al., "Ensuring an accurate result in an analytical instrumentation system—part 2: calibrating the analyzer", Swagelok Company, CORP-0148-02. First available online, Sep. 2, 2009, pp. 1-4.
International Search Report and Written Opinion of International Application No. PCT/US2017/036059 dated Sep. 1, 2017.
European Search Report and Written Opinion of European Application No. 17813793.1 dated Apr. 25, 2019.

* cited by examiner

| | Calibration | Reagent | Polarization Potential (E) V vs Ag/AgCl |
|---|---|---|---|
| The Conventional Method | Point 1 | Calibrator 1, Oxygen 150 mmHg | -0.75 V |
| | Point 2 | Calibrator 2, Oxygen 0 mmHg | -0.75 V |
| This Disclosure | Point 1 | Calibrator 1, Oxygen 150 mmHg | -0.75 V |
| | Point 2 | Same Calibrator 1 | 0 V or at Positive to the $O_2$ Reduction onset E |

FLUID ANALYZER FOR MEASURING A TARGET ANALYTE AND METHOD OF CALIBRATING AN AMPEROMETRIC SENSOR

This application claims priority to U.S. Provisional Application No. 62/351,377, filed Jun. 17, 2016 and U.S. Provisional Application No. 62/356,632, filed Jun. 30, 2016. Both disclosures of which are hereby incorporated by reference in their entirety.

BACKGROUND

There are several methods of measuring the oxygen concentration of liquids. For medical applications, electrochemical sensors have been developed and marketed. One instrument currently in use is the RAPIDPoint® 500 Analyzer, available from Siemens Healthcare Diagnostics, Inc. When measuring oxygen content of blood, a sensor of the type described in U.S. Pat. No. 5,387,329 is used. That sensor employs three electrodes, i.e. a working electrode, a reference electrode, and a counter electrode. The general principles of such three electrode sensors are described in U.S. Pat. No. 4,571,292. At the working electrode, oxygen is reduced to hydroxyl ions, while at the counter electrode the hydroxyl ions are oxidized to molecular oxygen. The sensors provide a reversible set of reactions and do not require consumption of the electrodes. The current measured when a voltage is applied across the working and counter/reference electrodes is correlated to the oxygen content of the sample.

Reference may be made to the description in U.S. Pat. No. 5,387,329 for details of a typical oxygen sensor. The three electrodes are thin metal strips deposited on a non-conductive substrate.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION

Figure 1:
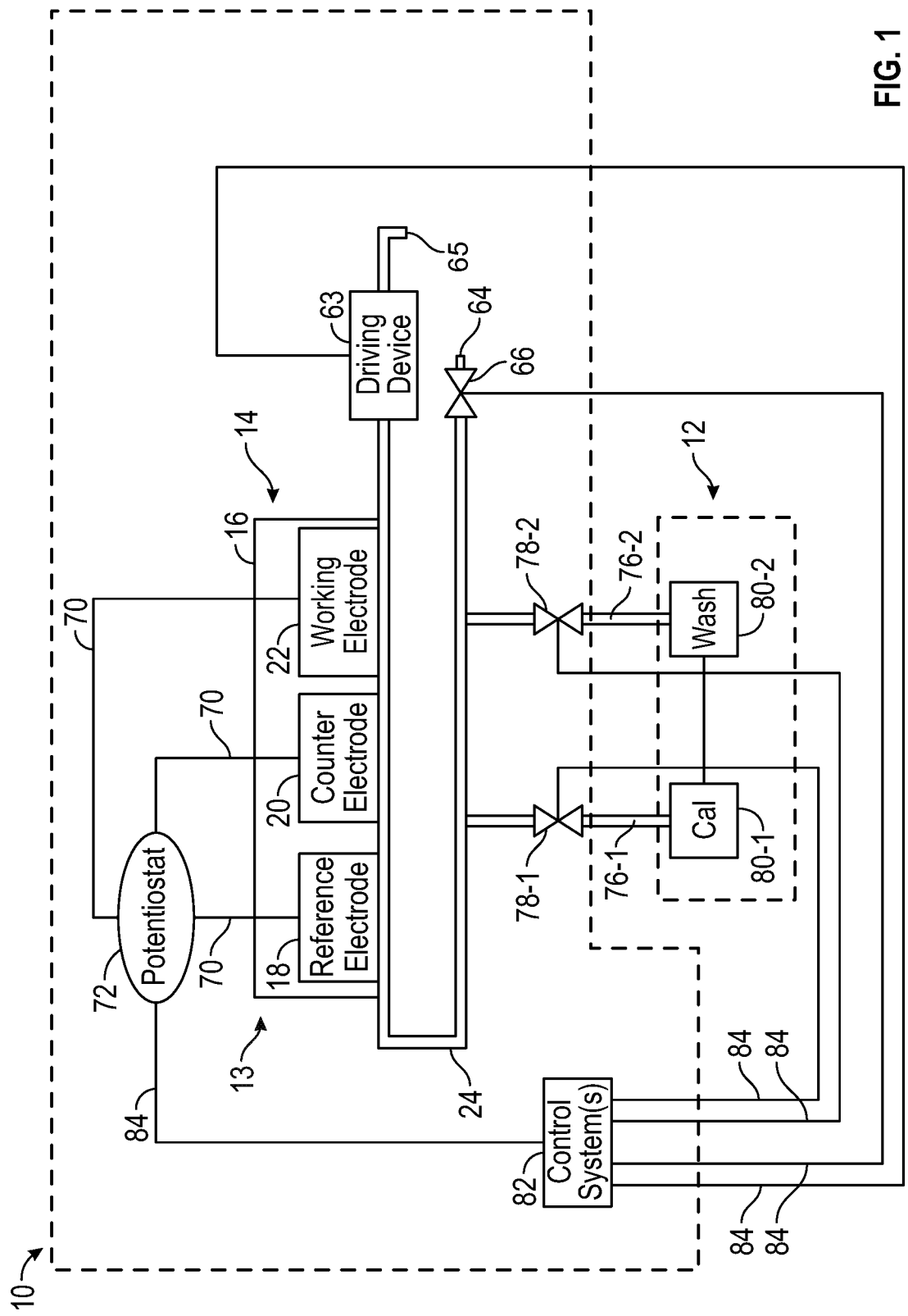
FIG. 1 illustrates a schematic diagram of an exemplary embodiment of a fluid analyzer comprising amperometric sensors and a calibration cartridge in accordance with the present disclosure.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The disclosure is capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements. Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the fluid analyzers and/or methods disclosed and/or claimed herein can be made and executed without undue experimentation in light of the present disclosure. While the fluid analyzer and methods of this presently disclosed and/or claimed inventive concept(s) have been described in terms of preferred embodiments, it will be apparent to those of skill in the art that variations may be applied to the fluid analyzers and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more, or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20%, or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "sample" as used herein will be understood to include any type of biological sample or non-biologic sample that may be utilized in accordance with the presently disclosed and/or claimed inventive concept(s). That is, the sample may be any fluidic sample and/or sample capable of being fluidic (e.g., a biological sample mixed with a fluidic substrate). Examples of biological samples that may be utilized include, but are not limited to, whole blood or any portion thereof (i.e., plasma or serum), saliva, sputum, cerebrospinal fluid (CSF), surgical drain fluid, skin, interstitial fluid, tears, mucus, urine, swabs, combinations, and the like. Examples of non-biologic samples include wastewater, industrial fluids and the like. It should be noted that although the present disclosure describes the use of the fluid analyzer to analyze a biological sample, one skilled in the art will appreciate that the concepts disclosed herein may be applied to any sample wherein a concentration of analyte may be determined, and as such, the present disclosure is not limited to biological samples. Exemplary target analytes include, but are not limited to oxygen, or a metabolite including, but not limited to, glucose, lactate, creatinine or the like.

The term "fluid" as used herein refers to a liquid or gas that can be passed through at least a portion of the fluid analyzer and analyzed by components of the fluid analyzer. The fluid may be a sample, a calibration reagent (e.g., fluid or gas), a wash fluid, or a quality control fluid.

The term "wetup" as used herein will be understood to refer to the hydration process from the installation of a sensor in a fluid analyzer to a point at which a stable signal is obtained out of calibration reagents.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like.

Software may include one or more computer readable instructions that when executed by one or more components cause the component to perform a specified function. It should be understood that the algorithms described herein may be stored on one or more non-transient memory. Exemplary non-transient memory may include random access memory, read only memory, flash memory, and/or the like. Such non-transient memory may be electrically based, optically based, and/or the like.

It is to be further understood that, as used herein, the term "user" is not limited to a human being, and may comprise, a computer, a server, a website, a processor, a network interface, a human, a user terminal, a virtual computer, combinations thereof, and the like, for example.

The term "calibration parameters" as used herein refers to a collection of data points or one or more functions used to derive a collection of data points that correlates the signals from the sensor to known analyte concentrations. The calibration parameters can be derived by a calibration algorithm, such as a linear algorithm, a spline-based algorithm, exponential algorithm, a least squares algorithm, a logarithmic algorithm, or the like that is configured to fit a function to at least two calibration points.

The term "calibration logic" as used herein refers to the program logic used by a processor within a control system to interpret data measured by one or more electrodes. In particular, the term "calibration logic" is the program logic of a control system used by a processor to interpret data from an amperometric sensor having at least a working electrode and a reference electrode.

Electrochemical sensors are widely used in in vitro diagnostic instruments. These electrochemical sensors including electrodes, which are fabricated from metals, from metal inks by screen-printing (thick film method) or from chemical vapor deposition of metal film (thin film method), generally require calibration. The calibration corrects the sensor-to-sensor variations in electrode size and surface area, change in chemical and biochemical activities during use life, electrical signal drift, etc. The oxygen sensor used in the Siemens Healthcare Point of Care (POC) RAPIDPoint 500 Blood Gas Analyzer has a screen-printed platinum working electrode, a silver/silver chloride reference electrode and a gold counter electrode.

The oxygen sensor is calibrated frequently by using one or more calibration reagents containing different oxygen tensions which are applied to the oxygen sensor in a sequential manner. As each of the calibration reagents are passed across the oxygen sensor, a reading is taken. When only one reading is obtained to calibrate the oxygen sensor, then the reading is taken at a non-zero oxygen level. When two or more readings are obtained to calibrate the oxygen sensor, then one of the readings can be indicative of a zero oxygen level. In any event, the one or more reading is used to generate a calibration curve which effectively serves to calibrate the oxygen sensor. It is difficult to precisely and accurately maintain a specific oxygen tension using an aqueous calibration solution. A common calibration scheme is a "two point calibration algorithm" whereby the first calibration reagent has an oxygen tension close to the ambient air oxygen tension (e.g. 150 mmHg) and the second calibration reagent has an oxygen tension of 0 mmHg. The second calibration reagent contains active ingredients sodium sulfite and a catalyst cobalt chloride. The sodium sulfite and cobalt chloride react with oxygen rapidly. As a result, oxygen in the second calibration reagent is scrubbed to zero and can be used as the 0 mmHg calibration point. Alternatively, the second calibration reagent can contain an oxygen tension greater than 0 mmHg and different from the oxygen tension of the first calibration reagent. However, it is advantageous to use a calibration reagent with a chemically-attained oxygen tension of 0 mmHg because aqueous calibrators for oxygen are not very robust.

The use of Cobalt chloride, however, is listed in the European Union's directives known as "Registration, Evaluation, Authorization, Restriction of Chemicals" (Reach) and "Restriction of Hazardous Substances" (RoHs) and will be banned in 2019. To comply with the REACH/RoHs regulation, the calibration method using a chemically derived oxygen tension of 0 mmHg for an oxygen sensor is required to be changed either to find a substitute to cobalt chloride or to develop a new calibration method.

On a blood gas analyzer such as the Siemens' RAPIDPoint 500 Blood Gas Analyzer, the oxygen sensor is polarized at −0.8 V vs Ag/AgCl for detecting oxygen tension in a patient blood sample by oxygen reduction. The oxygen sensor is calibrated with the use of two separate calibration reagents at oxygen tension 150 and 0 mmHg. When exposed to the first calibration reagent of oxygen tension 150 mmHg, a potentiostat measures the current that is the sum of two components, the faradaic current (oxygen reduction current) and the non-faradaic current (e.g., double layer charging current, etc). When exposed to the second calibration reagent (containing sodium sulfite and cobalt chloride (the catalyst)) of oxygen tension 0 mmHg, the potentiostat measures only the non-faradaic current. A linear calibration curve is thus derived from the linear regression of the 2-point calibration.

An electronic zero calibration that does not use Cobalt Chloride is one calibration method that has been applied to derive a non-chemical zero oxygen calibration point. This electronic zero calibration can be considered to be a calibration point that does not apply a calibration reagent to the oxygen sensor. Rather, electronic zero calibration measures the electronic background current of the electronic circuitry. The electronic background current of the blood gas analyzer in the absence of a calibration reagent is in fact not the true oxygen sensor background current measured in the conventional calibration that measures the output of the oxygen sensor when the calibration reagent having the 0 oxygen tension is applied. The current read by the instrument when the calibration reagent having the 0 oxygen tension is applied includes the oxygen sensor's non-faradaic current and the fluid analyzer's electronic circuitry background current.

The non-faradaic current does not involve any chemical reactions (charge transfer), but is due to the accumulation (or removal) of electrical charges on the electrodes and in the electrolyte solution near the electrodes. The oxygen sensor's non-faradaic and electronic circuitry background current can be determined at the manufacturing site provided the working electrodes of oxygen sensors have uniform electrode size and homogeneous chemical activity. Practically, electronic zero calibration is not applicable to some oxygen sensors.

Electronic zero calibration has been implemented for Siemens' RAPIDLab® 1200 Blood Gas Analyzer oxygen sensors. The platinum working electrode for the RAPIDLab 1200 oxygen sensor is uniformly and consistently defined by the diameter of a high purity platinum wire. With respect to the oxygen sensor in the Siemens' RAPIDPoint 500 Blood Gas Analyzer, the sensor's platinum working electrode is screen printed and does not have uniform size and area, due to the limitation of space resolution in the screen-printing process. Thus, the electronic zero calibration methodology would not work effectively to calibrate this fluid analyzer. Referring now to the Figures, and in particular to FIG. 1, shown therein is an illustration of an exemplary embodiment of a fluid analyzer 10 in combination with a calibration cartridge 12, and one or more electrochemical sensor 13. The one or more electrochemical sensor 13 can be implemented in the form of a cartridge that is connected to the fluid analyzer 10, for example, in the manner shown in FIG. 1. This 'sensor cartridge' can be removable or integrated into the fluid analyzer 10. The one or more electrochemical sensor 13 has at least one amperometric sensor 14. The fluid analyzer 10 may include a housing 16 supporting and/or encompassing at least a portion of the one or more electrochemical sensor 13.

This disclosure describes a new calibration method for the amperometric sensor 14. In one embodiment, the presently disclosed methodology is novel way of determining a zero oxygen tension calibration signal using one calibration reagent having an oxygen tension greater than 0 mmHg and that preferably does not contain cobalt chloride. As in the conventional calibration method using a zero oxygen tension calibration reagent discussed above, the presently disclosed calibration method detects the non-faradaic background current for the amperometric sensor 14 in the presence of the sample, taking into account any sensor-to-sensor variation caused by the variation in electrode size, surface area and surface chemical activity.

The amperometric sensor 14 generally comprises two or more electrodes 17, which are shown by way of example as a reference electrode 18, a counter electrode 20, and a working electrode 22. In one embodiment, the reference electrode 18, the counter electrode 20, and the working electrode 22 are selected so as to be able to produce an electrochemical reaction, i.e., reduction, in the presence of oxygen at a suitable voltage potential. In some embodiments, the reference electrode 18, the counter electrode 20, and the working electrode 22 are selected so as to be able to produce an electrochemical reaction with a target analyte or a reaction byproduct of the target analyte in a sample. In one embodiment, the reference electrode 18 can be constructed of silver/silver chloride, the working electrode 22 can be constructed of platinum, and the counter electrode 20 can be constructed of gold. However, it should be understood that the reference electrode 18, the counter electrode 20, and the working electrode 22 can be constructed of other materials including gold, platinum, silver, and combinations thereof.

Additionally, the electrochemical sensors 13 may comprise one or more additional electrodes (not pictured) for sensing other species within a fluid, such as a sample solution, quality control reagent, and/or calibration reagent. For example, the plurality of electrochemical sensors 13 may include ion selective electrodes for sensing other species including, but not limited to, potassium ions ($K^+$), sodium ions ($Na^+$), bicarbonate ions ($HCO_3^-$), and/or pH levels. Although FIG. 1 shows the reference electrode 18 being upstream of the counter electrode 20, and the working electrode 22, in one embodiment, the reference electrode 18 is downstream from the counter electrode 20 and the working electrode 22 (not pictured).

Referring to FIG. 1, the fluid analyzer 10 comprises a fluid channel 24, whereby a fluid, such as a sample, a quality control fluid, a wash fluid and/or a calibration reagent can pass through the fluid channel 24 to come into contact with the plurality of electrochemical sensors 13, including but not limited to the amperometric sensor 14. At least part of fluid channel 24 can be integrated into the above referenced 'sensor cartridge.' In one embodiment, at least the part of the fluid channel 24 which adjoins the electrochemical sensors 13 is part of the removable or integrated sensor cartridge.

Figure 2:
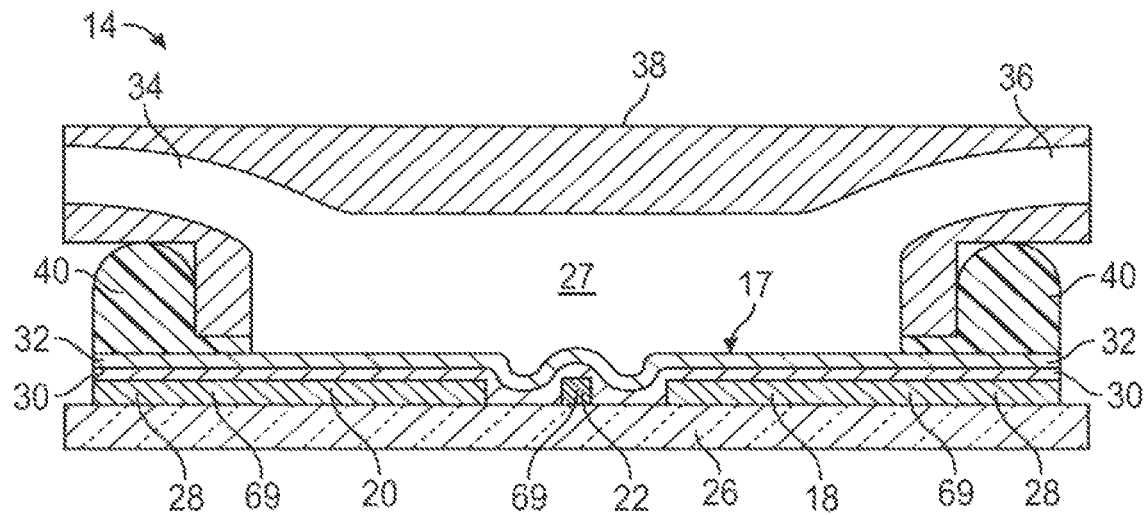
FIG. 2 illustrates a cross-sectional view of an exemplary embodiment of a prior art oxygen sensor including a working electrode, a reference electrode and a counter electrode that can be calibrated using the presently disclosed methodology.

Referring now to FIGS. 1 and 2, in one embodiment, the amperometric sensor 14 is assembled on a substrate 26 within the housing 16 defining a chamber 27. In this embodiment, the working electrode 22 is positioned between the reference electrode 18 and the counter electrode 20. The amperometric sensor 14 is provided with a dielectric layer 28. The substrate 26 can be constructed of a dielectric material, such as plastic, ceramic, silicon, etc. The dielectric layer 28 contains openings for one or more electrodes 17 of the amperometric sensor 14 including but not limited to the reference electrode 18, the counter electrode 20, and the working electrode 22. The electrodes 17 of the amperometric sensor 14 are covered by an electrolyte layer 30 (e.g., Nafion®) and a permeable membrane 32 (e.g., a copolymer). A fluid, such as the calibration reagent or a sample, enters the chamber 27 through an entry port 34 and exits the chamber 27 through an exit port 36. The housing 16 is provided with a cover 38 that encloses the amperometric sensor 14, and a gasket 40 that engages the permeable membrane 32, and the cover 38 to seal the chamber 27 and the entry port 34 and the exit port 36.

The fluid may pass through the fluid channel 24 and into the chamber 27 defined by the housing 16 supporting and/or encompassing the amperometric sensors 14 such that the fluid may assist in creating an electrochemical reaction between a target analyte or a reaction byproduct of a target analyte with the amperometric sensor 14.

Figure 3:
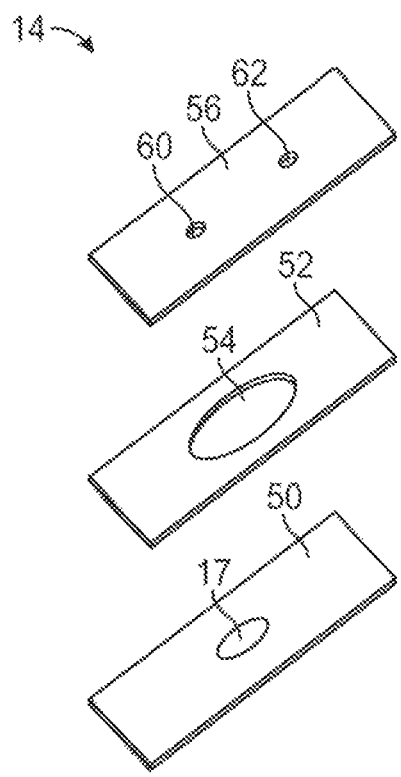
FIG. 3 illustrates an exploded view of another embodiment of a prior art oxygen sensor including a working electrode, a reference electrode and a counter electrode that can be calibrated using the presently disclosed methodology.

Shown in FIG. 3 is another embodiment of the amperometric sensor 14 that can be used in accordance with the present disclosure. In this embodiment, the amperometric sensor 14 is provided with the electrodes 17 including, but not limited to the reference electrode 18, the counter electrode 20, and the working electrode 22 on a substrate 50. The substrate 50 extends outwardly from the electrodes 17. The amperometric sensor 14 is also provided with a gasket 52 having an opening 54 sized and dimensioned to be larger than the area of the substrate 50 encompassed by the electrodes 17. The gasket 52 is positioned on the substrate 50 such that the gasket 52 does not overlap with the electrodes 17. Rather, the gasket 52 engages the substrate 50 around the electrodes 17. The amperometric sensor 14 also includes a cover 56 that is positioned on the gasket 52 such that the gasket 52 is between the substrate 50 and the cover 56. The opening 54 within the gasket 52, in conjunction with the cover 56 and the substrate 50 forms a chamber (not shown) through which the fluid can pass and interact with the electrodes 17. An entry port 60 and an exit port 62 can be formed within the cover 56 to permit the fluid to enter and exit the chamber.

Returning to FIG. 1, a fluid may flow through the fluid channel 24 by a driving force provided by a driving device 63. The driving force may include, but is not limited to, capillary force, pressure, gravity, vacuum, electrokinesis, and/or the like. The driving device 63 may be, for example but without limitation, a pump.

The sample can be introduced into the fluid channel 24 via a sample injection port 64. The sample injection port 64 may be in communication with a valve 66 that can be manually or machine opened and/or closed to allow and/or prevent the sample from entering the fluid channel 24. The sample can be manually injected or injected by a machine into the sample injection port 64. Once the sensor cartridge (which is comprised of electrochemical sensors 13 and at least part of the flow channel 24) is removably inserted or integrated into the machine the sample can enter via valve 66, flow through flow channel 24 and exit via exit port 65. Similarly, calibration reagent and wash fluid can enter via valves 78-1 and 78-2, respectively, and exit via exit port 65.

In some embodiments, the fluid channel 24 may be a hollow channel. The fluid channel 24 also may comprise a waste output 65, whereby the fluid exits the fluid channel 24 after contacting at least one, and preferably all, of the plurality of amperometric sensors 14.

Referring to FIG. 2, for example, the fluid channel 24 may deliver the sample to the chamber 27. The chamber 27 indirectly intersects with the amperometric sensor 14, including, for example but without limitation, the reference electrode 18, the counter electrode 20, and the one or more reference electrodes 18 via the electrolyte layer 30 and the permeable membrane 32.

In some embodiments, the chamber 27 may be a hollow channel.

In some embodiments, the substrates 26 and 50 may be formed of a rigid material. Alternatively, the substrates 26 and 50, or a portion thereof, may be formed of a flexible material.

The substrates 26 and 50 may be formed of materials including, but not limited to, plastic, ceramic, glass, and/or any material capable of containing electrodes 17. For example, in some embodiments, the substrates 26 and 50 may be formed of polyethylene terephthalate (PET).

As shown in FIG. 2, the electrodes for the plurality of electrochemical sensors 13 including, for example, the reference electrode 18, the counter electrode 20, and the working electrode 22 may include one or more conductive layer(s) 69. The conductive layer(s) 69 may be formed of any suitable conductive material including, but not limited to, carbon, silver, silver chloride, gold, platinum, palladium, and/or the like. The conductive layer(s) 69 may be sputtered, electroplated, screen printed, inkjet printed, bonded and/or any other technique capable of applying conductive material to the housing 16 associated with fabrication of the amperometric sensors 14.

In some embodiments, the conductive layer(s) 69 may be formed by laser ablation of a gold sputtered metal film on a backing. Alternatively, in some embodiments, the conductive layer(s) 69 may be formed of localized positioning of a carbon within the housing 16. As illustrated in FIGS. 1 and 2, the electrodes 17 including, for example but without limitation, the reference electrode 18, the counter electrode 20, and the working electrode 22 may also include leads 70 for connection to a potentiostat 72.

Generally, the potentiostat 72 receives signals generated by the reference electrode 18, the counter electrode 20, and the working electrode 22 in contact with a fluid comprising a target analyte such as oxygen within a sample, a quality control reagent, and/or a calibration reagent and transforms the signals into information to correlate the electric potentials to the amount of target analyte in the fluid. The potentiostat 72 is an electronic instrument that measures a current between two electrodes of a plurality of electrodes 17, and controls a voltage difference between two electrodes of the plurality of electrodes 17. For example, when the amperometric sensor 14 includes the reference electrode 18 and the working electrode 22, the potentiostat 72 measures the current between the reference electrode 18 and the working electrode 22 and controls a voltage difference between the working electrode 22 and the reference electrode 18. In one embodiment in which the amperometric sensor 14 includes the counter electrode 20, the potentiostat 72 measures the current flow between the working electrode 22 and the counter electrode 20 and controls a voltage difference between the working electrode 22 and the reference electrode 18. The reference electrode 18, the counter electrode 20 and the working electrode 22 provide a reversible or irreversible set of reactions and do not require consumption of the electrodes 17. The current measured by the potentiostat 72 when a voltage is applied across the working and reference electrodes 22 and 18 is correlated to the target analyte content of the fluid.

In some embodiments, the fluid analyzer 10 may further comprise one or more calibration reagent injection ports 76-1 and 76-2 which may be in fluidic communication with the fluid channel 24. The calibration reagent injection ports 76-1 and 76-2 may also be in communication with valves 78-1, and 78-2 that can be manually or machine opened and/or closed to allow and/or prevent one or more calibration reagents and/or wash fluids from entering the fluid channel 24. The valves 78-1, and 78-2 can be automated valves that can open or close upon receipt of a suitable control signal.

In some embodiments, the one or more calibration reagent injection ports 76-1, and 76-2 can be in fluidic communication with the calibration cartridge 12 comprising one or more calibration reagents.

In some embodiments, the calibration cartridge 12 comprises at least two reservoirs 80-1, and 80-2. The reservoir 80-1 contains a calibration reagent having a known target analyte level, e.g., oxygen tension (e.g., 150 mmHg), and the reservoir 80-2 contains a wash fluid. The wash fluid may be an aqueous wash reagent typically containing a surfactant to remove the calibration reagent and/or the sample from the interior of the housing 16 abutting the chamber 27, for example. In some non-limiting embodiments, the calibration cartridge 12 comprises only one reservoir 80-1 containing a calibration reagent having a known oxygen tension.

Referring again to FIG. 1, the potentiostat 72, driving device 63, and valves 66, 78-1, and 78-2, may be in communication with a control system 82 via signal paths 84. The signal paths 84, as shown in FIG. 1, may be, for example but without limitation, one or more cables which convey the data produced by the potentiostat 72 to the control system 82 and/or information, signals, commands from the control system 82 to the valves 66, 78-1, and 78-2, in electronic form and/or via a network as described in detail herein. The control system 82 may be a system or systems that are able to embody and/or execute the logic of the processes described herein. Logic embodied in the form of software instructions and/or firmware may be executed on any appropriate hardware. For example, logic embodied in the form of software instructions and/or firmware may be executed on dedicated system or systems, on a personal computer system, on a distributed processing computer system, and/or the like. In some embodiments, logic may be implemented in a stand-alone environment operating on a single computer system and/or logic may be implemented in a networked environment such as a distributed system using multiple computers and/or processors.

In one embodiment, the calibration cartridge 12 comprising one or more calibration reagents can be in fluidic communication with one or more quality control fluid injection ports (not pictured) that are in fluidic communication with the fluid channel 24. In one embodiment, the quality control injection port(s) (not pictured) can be in fluidic communication with one or more quality control fluid valves (not pictured), whereby the quality control fluid valve(s) (not pictured) can be manually or machine opened and/or closed to allow and/or prevent the quality control fluid(s) from entering the fluid channel 24. The quality control fluid valves (not pictured) can be automated valves that can open or close upon receipt of a suitable control signal.

Figure 4:
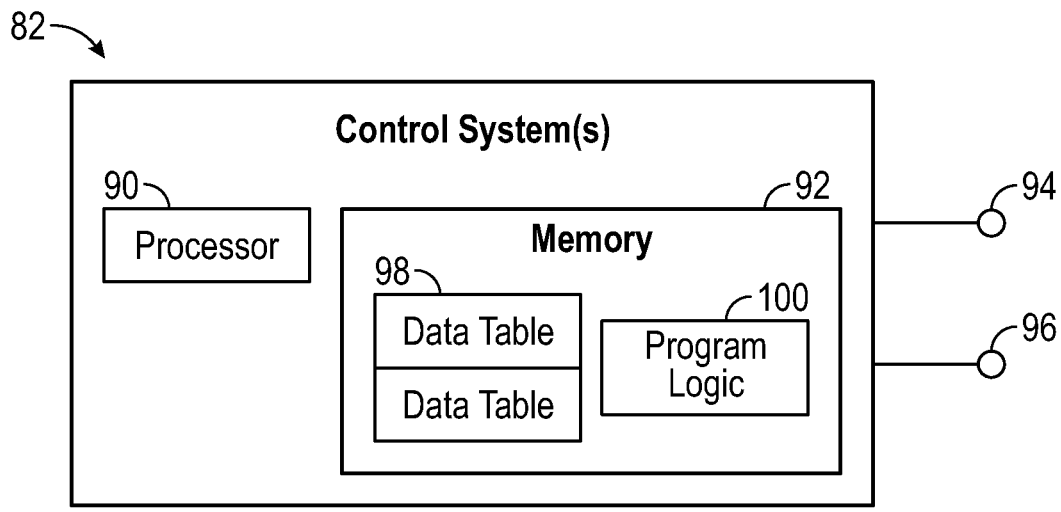
FIG. 4 is a block diagram of a control system of the fluid analyzer depicted in FIG. 1.

Shown in FIG. 4 is a block diagram of the control system 82 which may include one or more processors 90 (hereinafter "processor 90") working together, or independently, to execute processor executable code, one or more memories 92 (hereinafter "memory 92") capable of storing processor executable code, one or more input devices 94 (hereinafter "input device 94"), and one or more output devices 96 (hereinafter "output device 96"). When executed, the processor executable code causes the processor 90 to: control the automated valve 78-1 to pass the calibration reagent through the fluid channel 24 to the working electrode 22, and the reference electrode 18 (and the counter electrode 20 when included in the amperometric sensor 14); control the potentiostat 72 to apply a first voltage potential to the working and reference electrodes 22 and 18 sufficient to induce an electrochemical reaction in the sample of the calibration reagent and receive a first reading from the potentiostat 72; control the potentiostat 72 to apply a second voltage potential to the working and reference electrodes 22 and 18 insufficient to induce an electrochemical reaction in the sample of the calibration reagent and receive a second reading from the potentiostat 72; calculate calibration parameters using the first reading, the second reading and a multi-calibration algorithm; and measure the target analyte content within a fluid sample using the calibration parameters.

Each element of the control system 82 may be partially or completely network-based or cloud based, and may or may not be located in a single physical location. In some embodiments, the processor 90 may communicate with the potentiostat 72, driving device 63, and/or one or more valves 66, 78-1, and 78-2 via a network. As used herein, the terms "network-based", "cloud-based", and any variations thereof, are intended to include the provision of configurable computational resources on demand via interfacing with a computer and/or computer network, with software and/or data at least partially located on the computer and/or computer network. The network may permit bi-directional communication of information and/or data between the processor 90. The network may interface with the processor 90 and the potentiostat 72, driving device 63, and/or one or more valves 66, 78-1, and 78-2, in a variety of ways. For example, but without limitation, the network may interface by optical and/or electronic interfaces, and/or may use a plurality of network topographies and/or protocols including, but not limited to, Ethernet, TCP/IP, circuit switched paths, combinations thereof, and/or the like. For example, in some embodiments, the network may be implemented as the World Wide Web (or Internet), a local area network (LAN), a wide area network (WAN), a metropolitan network, a wireless network, a cellular network, a GSM-network, a CDMA network, a 3G network, a 4G network, a satellite network, a radio network, an optical network, a cable network, a public switch telephone network, an Ethernet network, combinations thereof, and/or the like. Additionally, the network may use a variety of protocols to permit bi-directional interface and/or communication of data and/or information between the processor 90 and the potentiostat 72, driving device 63, and/or one or more valves 66, 78-1, and 78-2.

In some embodiments, the network may be the Internet and/or other network. For example, if the network is the Internet, a primary user interface of the control system 82 may be delivered through a series of web pages (e.g., target analyte concentration determination webpages). It should be noted that the primary user interface of the control system 82 may also be another type of interface including, but not limited to, a Windows-based application.

The processor 90 may be implemented as a single processor or multiple processors working together, or independently, to execute the logic as described herein. It is to be understood, that in certain embodiments when using more than one processor 90, the processors 90 may be located remotely from one another, located in the same location, or comprising a unitary multi-core processor. The processor 90 may be capable of reading and/or executing processor executable code and/or capable of creating, manipulating, retrieving, altering and/or storing data structure into the memory 92.

Exemplary embodiments of the processor 90 may include, but are not limited to, a digital signal processor (DSP), a central processing unit (CPU), a field programmable gate array (FPGA), a microprocessor, a multi-core processor, combinations thereof, and/or the like, for example. In some embodiments, additional processors 90 may include, but are not limited to, implementation as a personal computer, a cellular telephone, a smart phone, network-capable television set, a television set-top box, a tablet, an e-book reader, a laptop computer, a desktop computer, a network-capable handheld device, a video game console, a server, a digital video recorder, a DVD-player, a Blu-Ray player, and/or combinations thereof, for example.

The processor 90 may be capable of communicating with the memory 92 via a path (e.g., data bus). The processor 90 may also be capable of communicating with the input device 94 and/or the output device 96.

The processor 90 may be capable of interfacing and/or communicating with the potentiostat 72, driving device 63, and/or one or more valves 66, 78-1, and 78-2. For example, the processor 90 may be capable of communicating by exchanging signals (e.g., analog, digital, optical, and/or the like) using a network protocol.

The memory 92 may be capable of storing processor executable code. Additionally, the memory 92 may be implemented as a conventional non-transient memory, such as, for example, random access memory (RAM), a CD-ROM, a hard drive, a solid state drive, a flash drive, a memory card, a DVD-ROM, a floppy disk, an optical drive, combinations thereof, and/or the like.

In some embodiments, the memory 92 may be located in the same physical location as the processor 90, and/or the memory 92 may be located remotely from the processor 90. For example, the memory 92 may be located remotely from the processor 90 and communicate with other processors via the network. Additionally, when more than one memory 92 is used, a first memory may be located in the same physical location as the processor 90, and additional memories 92 may be located in a remote physical location from the processor 90. Additionally, the memory 92 may be implemented as a "cloud memory" (i.e., one or more memories 92 may be partially or completely based on or accessed using the network).

The input device 94 may be capable of receiving information input from a user and/or processor(s) 90, and may be capable of transmitting such information to the processor 90, network, and/or potentiostat 72, driving device 63, and/or one or more valves 66, 78-1, and 78-2. The input device 94 may include, but is not limited to, implementation as a keyboard, touchscreen, mouse, trackball, microphone, fingerprint reader, infrared port, slide-out keyboard, flip-out keyboard, cell phone, PDA, video game controller, remote control, fax machine, network interface, combinations thereof, and the like, for example.

The output device 96 may be capable of outputting information in a form perceivable by a user and/or processors(s) 90. For example, the output device 96 may include, but is not limited to, implementation as a computer monitor, a screen, a touchscreen, a speaker, a website, a television set, a smart phone, a PDA, a cell phone, a fax machine, a printer, a laptop computer, combinations thereof, and/or the like, for example. It is to be understood that in some exemplary embodiments, the input device 94 and the output device 96 may be implemented as a single device, such as, for example, a touchscreen or a tablet. It is to be further understood that as used herein the term user is not limited to a human being, and may comprise, a computer, a server, a website, a processor, a network interface, a human, a user terminal, a virtual computer, combinations thereof, and/or the like, for example.

The memory 92 may store processor executable code and/or information comprising one or more databases and/or data tables 98 and program logic 100 (also referred to herein as "calibration logic"). In some embodiments, the processor executable code may be stored as a data structure, such as a database and/or a data table 98, for example. In some embodiments, outputs of the potentiostat 72, driving device 63, and/or one or more valves 66, 78-1, and 78-2 may be stored in one or more databases and/or data tables 98 within the memory 92.

Figure 5:
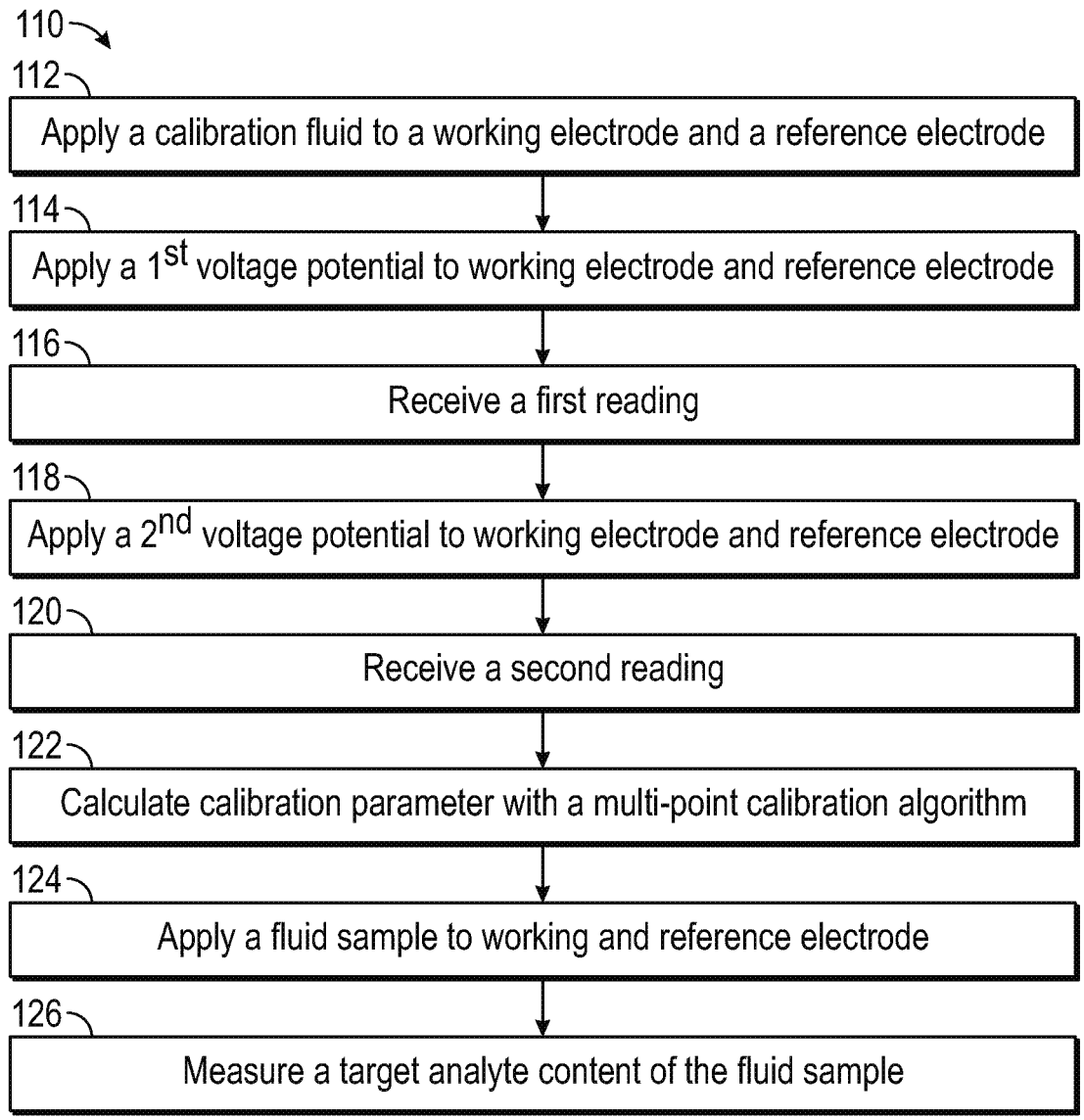
FIG. 5 illustrates a flow chart of an exemplary two-point calibration method for calibrating an oxygen sensor utilizing a single calibration reagent in accordance with the presently disclosed methodology.

FIG. 5 illustrates a process 110 for calibrating the processor 90 to properly interpret signals from the amperometric sensor 14 in the fluid analyzer 10. This method can be run periodically by the processor 90 to ensure that the amperometric sensor 14 is providing accurate results. The presently disclosed methodology is a true multi-point calibration that calibrates the amperometric sensor 14 by collecting data from the amperometric sensor 14 at two or more preselected and different target analyte concentrations, e.g., at a first oxygen tension of the calibration reagent, and a second oxygen tension that is electrochemically simulated. In one example, the oxygen tension of the calibration reagent is 150 mmHg and the electrochemically simulated oxygen tension is 0 mmHg. In some embodiments, the calibration reagent does not contain cobalt chloride. As in the conventional multi-point calibration method using two separate calibration reagents, the presently disclosed calibration method may detect the non-faradaic background current for the amperometric sensor 14, taking into account any sensor-to-sensor variation caused by the variation in electrode size, surface area and surface chemical activity. It should be understood that the counter electrode 20 is optional and may be omitted in certain embodiments.

In some embodiments of the presently disclosed methodology, the calibration cartridge 12 and a sensor cartridge containing the electrochemical sensors 13, including the amperometric sensor 14, is mounted to the fluid analyzer 10 such that fluid reservoir 80-1 is fluidly connected to the calibration reagent injection port 76-1, and the amperometric sensor 14 is electrically connected to the potentiostat 72. At a step 112, a calibration reagent having a predetermined target analyte level is applied to the reference electrode 18, the counter electrode 20, and the working electrode 22. This can be accomplished by the control system 82 opening the automated valve 78-1 and actuating the driving device 63 to pass the calibration reagent from the fluid reservoir 80-1 through the fluid channel 24 to the chamber 27, for example. When a sufficient amount of calibration reagent is within the chamber 27, the control system 82 closes the automated valve 78-1 and de-actuates the driving device 63. Once the calibration reagent is within the chamber 27 and applied to the reference electrode 18, the counter electrode 20 and the working electrode 22, at a step 114 the control system 82 provides a signal to the potentiostat 72 to cause the potentiostat 72 to apply a first voltage potential to the working electrode 22, and the reference electrode 18 sufficient to induce an electrochemical reaction in the sample of the calibration reagent. At a step 116, the potentiostat 72 then receives a first reading from the working electrode 22, and the counter electrode indicative of the faradaic and non-faradaic current generated by an oxidation/reduction electrochemical reaction occurring between the working electrode 22, the counter electrode 20, the reference electrode 18 and the target analyte, e.g., oxygen, within the calibration reagent. At a step 118, the control system 82 then sends a signal to the potentiostat 72 to cause the potentiostat 72 to apply a second voltage potential to the working electrode 22 and the reference electrode 18 insufficient to induce an electrochemical reaction in the calibration reagent. The second voltage potential can be determined and/or applied using a voltage potential stepping technique in which a series of sequentially greater or smaller voltage potentials are applied. When the current from the working electrode 22 and, the counter electrode 20 levels off, then it is determined that the applied voltage potential is insufficient to induce an electrochemical reaction in the calibration reagent. At a step 120, the potentiostat 72 receives a second reading from the working electrode 22 and the counter electrode 20 indicative of non-faradaic current. The steps 114 and 116 can occur before or after the steps 118 and 120. The potentiostat 72 transmits data indicative of the first reading and the second reading to the control system 82, which at a step 122 uses the processor 90 to calculate calibration parameters using the first reading, the second reading and a multi-point calibration algorithm. The calibration parameters can be stored within the data table 98 within the memory 92 and used for measuring the target analyte content of fluids. The control system 82 then opens/closes the automated valve 78-2 and actuates/deactuates the driving device 63 so as to pass the wash fluid through the fluid channel 24 and the chamber 27 to wash the amperometric sensor 14. Thereafter, the fluid analyzer 10 can be used to apply a fluid sample having an unknown target analyte content to the working electrode 22, the counter electrode 20 and the reference electrode 18, at a step 124 and then measure a target analyte content of the fluid sample with the calibration parameters at a step 126. The steps 124 and 126 can then be repeated to measure the target analyte content of fluid samples before the steps 112, 114, 116, 118, 120 and 122 are repeated to recalibrate the amperometric sensor 14 to ensure accurate results.

EXAMPLES

Examples are provided hereinbelow. However, the presently disclosed and/or claimed inventive concept(s) is to be understood to not be limited in its application to the specific experimentation, results, and procedures disclosed hereinbelow. Rather, the Examples are provided as various embodiments and are meant to be exemplary, not exhaustive.

Example 1

An amperometric sensor for a fluid analyzer that was similar in construction and function to the amperometric sensor 14 depicted in FIG. 2 was calibrated using the procedure outlined above.

In particular, a voltage potential stepping technique was used to polarize the amperometric sensor at −0.75 V and 0 V in the presence of a calibration reagent having an oxygen tension 150 of mmHg. Table 1 of FIG. 6 summarizes the inputs to the amperometric sensor in the conventional calibration method and the presently disclosed calibration method.

For comparison purposes, the presently disclosed calibration method and the conventional method are denoted as having "Point 1" and "Point 2" measurements. With the presently disclosed calibration methodology, the amperometric sensor is calibrated in calibration reagent 1 with oxygen tension 150 mmHg at the normal polarization potential, i.e., −0.75 V. The point 2 calibration is performed with the amperometric sensor in the same calibration reagent, but a positive voltage potential step is applied to the amperometric sensor from the normal polarization potential to an oxygen reduction onset potential. In this example, the oxygen reduction onset potential was 0 V.

Figures 6, 7:
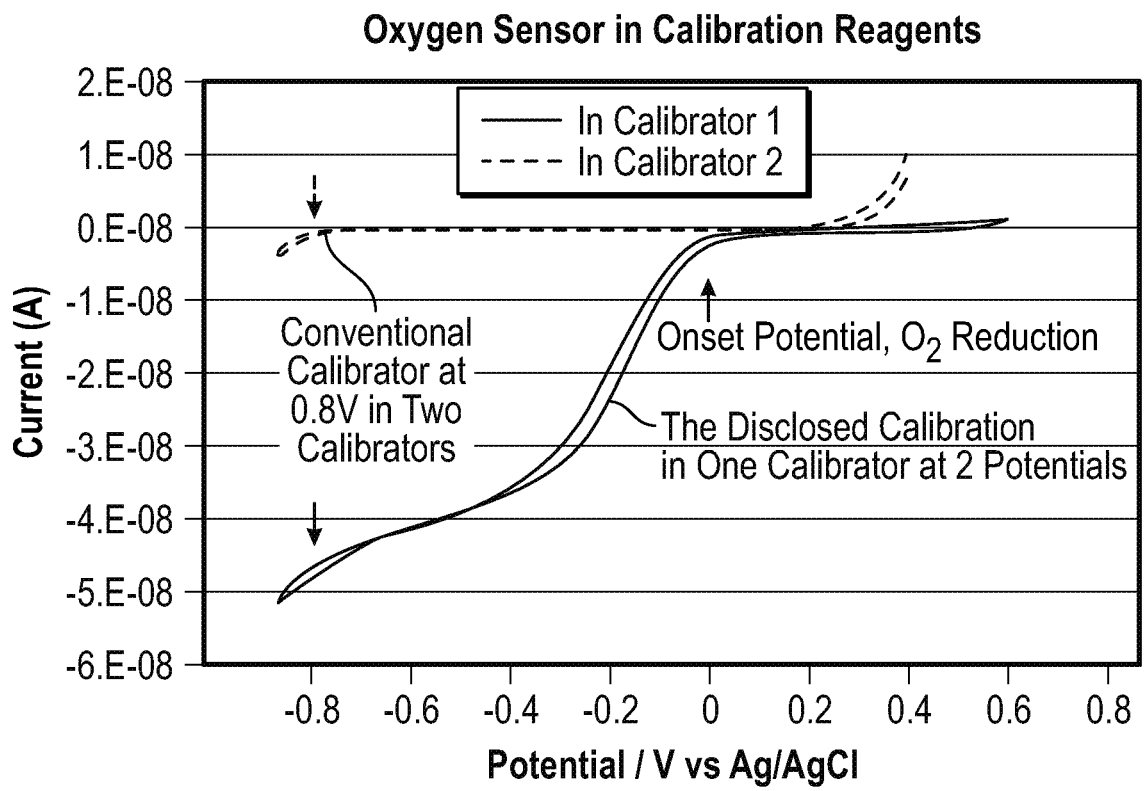
FIG. 6 is an illustration of TABLE 1 showing a comparison between the conventional two-point calibration methodology using two separate calibration reagents and the presently disclosed calibration methodology using a single calibration reagent.
FIG. 7 is a graph showing a comparison of various applied voltages and induced currents in the conventional two point calibration methodology and the presently disclosed two point calibration methodology.

FIG. 7 shows a cyclic voltammograms of oxygen reduction by the amperometric sensor in the conventional calibration reagent 1 and calibration reagent 2. From the cyclic voltammogram of oxygen reduction in the calibration reagent 1 (the solid curve in FIG. 7), the oxygen reduction current starts to rise (negative current) as the electrode potential is scanned in a negative direction and past the potential 0 V. The onset potential of oxygen reduction is defined by definition as the potential at which oxygen reduction starts. The oxygen cannot be reduced or detected at the potentials positive to the oxygen reduction onset potential. This experiment shows that one can turn off or turn on oxygen reduction electrochemically by polarizing the amperometric sensor at potentials below or above the oxygen reduction onset potential. The conventional calibration method removes oxygen in the calibration reagent 2 by chemically scrubbing oxygen by the use of sulfite and cobalt. By contrast, the presently disclosed calibration method turns off oxygen reduction electrochemically during an oxygen presence in calibration reagent 1 (e.g., oxygen tension 150 mmHg). The effect of electrochemically turning off oxygen reduction simulates the results obtained during the conventional calibration methodology that applies the second calibration reagent having an absence of oxygen to the amperometric sensor. The test results show that both methods lead to the same result. In this example, the potentiostat measures the amperometric sensor's non-faradaic background current, more accurately, the sum of the current oxygen sensor's non-faradaic background current and the fluid analyzer's electronic background current. The experimental data demonstrates that the measured oxygen sensor background current by the presently disclosed calibration method is equivalent to the oxygen sensor background current measured in the conventional calibration method, as shown in FIG. 7.

Figure 8:
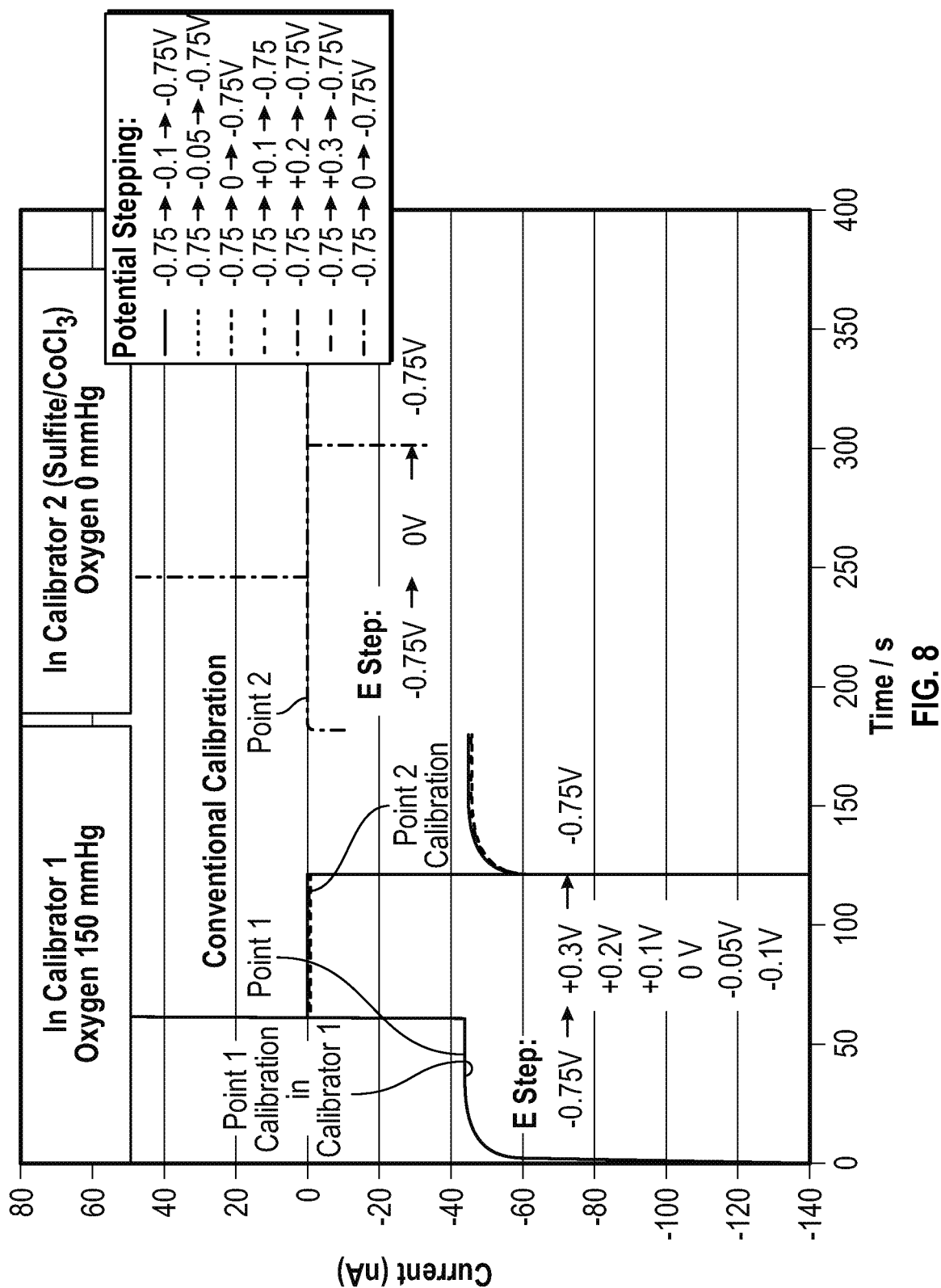
FIG. 8 is another graph of a comparison over time of the conventional two point calibration methodology and the presently disclosed two point calibration methodology showing that measured oxygen sensor background current determined by the presently disclosed two point calibration methodology is equivalent to the oxygen sensor background current measured in the conventional two point calibration method.
Figure 9:
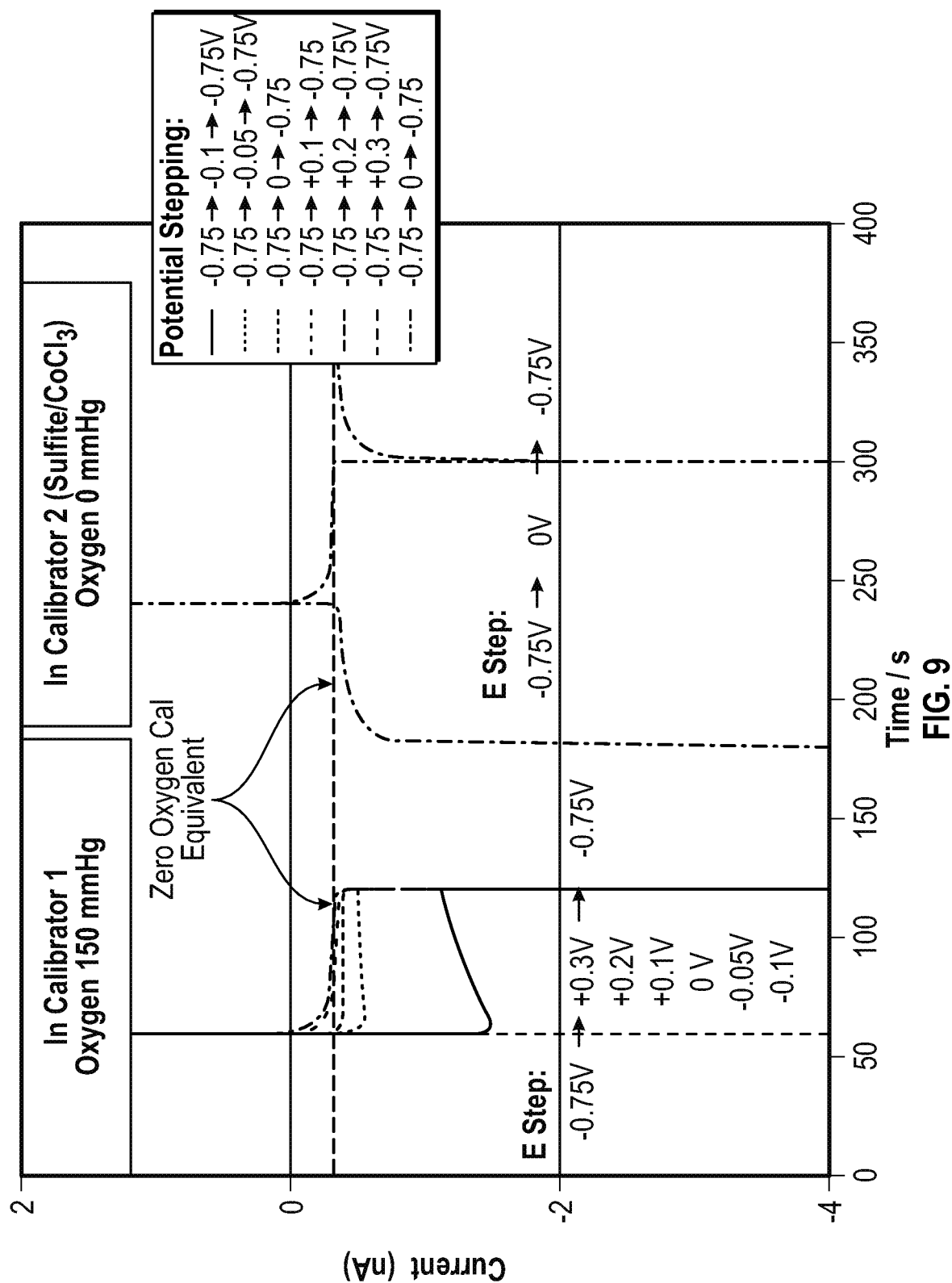
FIG. 9 is a graph that is similar to the graph of FIG. 8, except that FIG. 9 includes a lower current scale to illustrate that the oxygen sensor background currents are equivalent in the presently disclosed and conventional calibration methods.

Shown in FIG. 8 is additional experimental data of the presently disclosed and conventional calibration methodologies. FIG. 8 shows a series of current measurements over time in the presently disclosed calibration method compared to the current in the conventional calibration method. FIG. 9 shows the same curves shown in FIG. 8 but with a lower current scale. As shown in FIGS. 8 and 9, the amperometric sensor background currents are equivalent in the presently disclosed and conventional calibration methods. In the experiment, the amperometric sensor was first calibrated by the conventional calibration method. The amperometric sensor was first polarized by applying a −0.75 V potential between the working and the reference electrode. In running the point 1 calibration, the calibration reagent 1 (oxygen tension 150 mmHg) was pumped into the chamber of the amperometric sensor. In the point 2 calibration procedure, the calibration reagent 2 (oxygen tension 0 mmHg) was pumped into the chamber of the amperometric sensor. The −0.75V voltage potential between the working and the reference electrodes was maintained and the currents were recorded as a function of time (FIG. 8). After the conventional calibration procedure, the same amperometric sensor was calibrated using the presently disclosed calibration methodology in which the calibration reagent 1 was pumped into the chamber of the amperometric sensor. The potential of the amperometric sensor was stepped to the potentials near the oxygen reduction onset potentials, −0.1, −0.05, 0, +0.1, +0.2 and +0.3 V, respectively. The current was measured continuously. At the stepped potential −0.1 V, the measured current was low but not quite close to the expected background current level, indicating the oxygen reduction was not completely turned off at −0.1 V. The oxygen reduction current continued decreasing as the stepped potentials moved in a positive direction towards to the oxygen reduction onset potential (see FIG. 9). The current of the amperometric sensor approached the background current of the conventional calibration measured in the calibration reagent 2 (oxygen tension 0 mmHg). When the stepped potential passed 0 V, it was determined that in this experiment, the potential −0 V was the onset potential of oxygen reduction. Furthermore, the current did not increase and remained at the background current as the amperometric sensor potential was stepped to potentials positive to the oxygen reduction onset potential, indicating that the measured background current was the non-faradaic current of the amperometric sensor. This potential stepping technique also determined the oxygen reduction onset potential, which was in agreement to the oxygen reduction onset potential identified from the cyclic voltammogram (see FIG. 7). After the data was obtained for the 2-point calibration in the calibration reagent 1, the potential of the amperometric sensor was returned back to the original polarization potential, −0.75 V.

The presently disclosed calibration method allows the amperometric sensor to be calibrated at two points, oxygen tension of 150 mmHg and an effective oxygen tension of 0 mmHg, in one calibration reagent containing an oxygen tension above 0 mmHg. The presently disclosed calibration method reduces the number of calibration reagents needed to calibrate the amperometric sensor as compared to the conventional calibration methodology, resulting in a cost reduction for calibrator reagent manufacturing. Furthermore, the presently disclosed calibration method eliminates the use of cobalt chloride, which ensures that fluid analyzers constructed in accordance with the present disclosure will be in compliance with the REACH/RoHs regulation.

In one illustrative embodiment, the present disclosure describes a non-transitory computer readable storing processor executable code that when executed by a processor causes the processor to: control the potentiostat 72 to apply a first voltage potential sufficient to induce a first electrochemical reaction of a target analyte or a reaction byproduct of the target analyte in a sample of the calibration reagent and receive a first reading from the potentiostat 72; control the potentiostat 72 to apply a second voltage potential insufficient to induce a second electrochemical reaction of the target analyte or a reaction byproduct of the target analyte in the sample of the calibration reagent and receive a second reading from the potentiostat 72; calculate calibration parameters using the first reading, the second reading and a multi-point calibration algorithm.

In some embodiments, the processor executable code causes the processor to measure a target analyte concentration within a fluid sample using the calibration parameters.

In some embodiments, the present disclosure describes the control system 82 having one or more processor 90 executing processor executable code to cause the one or more processor to control the potentiostat 72 to apply a first voltage potential sufficient to induce a first electrochemical reaction of a target analyte or a reaction byproduct of the target analyte in a sample of the calibration reagent and receive a first reading from the potentiostat 72; control the potentiostat 72 to apply a second voltage potential insufficient to induce a second electrochemical reaction of the target analyte or a reaction byproduct of the target analyte in the sample of the calibration reagent and receive a second reading from the potentiostat 72; calculate calibration parameters using the first reading, the second reading and a multi-point calibration algorithm.

In some embodiments, the processor executes processor executable code to measure a target analyte concentration within a fluid sample using the calibration parameters.

Therefore, in accordance with the presently disclosed and/or claimed inventive concept(s), there have been provided the fluid analyzer 10 for detecting a level of oxygen within a sample that calibrates the amperometric sensor 14 using a single calibration reagent having an oxygen tension above 0 mmHg, e.g., 150 mmHg up to 800 mmHg. Although the presently disclosed and/or claimed inventive concept(s) has been described in conjunction with the specific drawings, experimentation, results, and language set forth herein above, it is evident that many alternatives, modifications, and variations will be apparent to those of ordinary skill in the art. Accordingly, it is intended to embrace all such alternatives, modifications, and variations that fall within the spirit and broad scope of the presently disclosed and/or claimed inventive concept(s).

What is claimed is:

1. A fluid analyzer for analyzing a fluid sample, comprising:
    a potentiostat, when in electrical communication with two or more electrodes of an amperometric sensor, configured to measure signals generated by at least two of the two or more electrodes, and to control a voltage difference between at least two of the two or more electrodes;
    at least one calibration injection port adapted to receive a calibration reagent having a predetermined target analyte level of a target analyte;
    at least one automated valve communicating with the at least one calibration injection port and being openable and closable to pass one or more samples of the calibration reagent; and
    a control system having a processor executing processor executable code that when executed causes the processor to:
    control the at least one automated valve to pass the calibration reagent through a fluid channel to the two or more electrodes;
    control the potentiostat to apply a first voltage potential sufficient to induce a first electrochemical reaction of the target analyte or a reaction byproduct of the target analyte in a sample of the calibration reagent and receive a first reading from the potentiostat;
    control the potentiostat to apply a second voltage potential insufficient to induce a second electrochemical reaction of the target analyte or the reaction byproduct of the target analyte in the sample of the calibration reagent and receive a second reading from the potentiostat;
    calculate calibration parameters using the first reading, the second reading and a multi-point calibration algorithm; and
    measure a target analyte concentration within the fluid sample using the calibration parameters.

2. The fluid analyzer of claim 1, wherein the target analyte is oxygen, and wherein the predetermined target analyte level is characterized as an oxygen tension within a range from 0 to 800 mmHg.

3. The fluid analyzer of claim 1, wherein the multi-point calibration algorithm includes a zero target analyte calibration point.

4. The fluid analyzer of claim 1, wherein the calibration parameters establish a correlation between the first reading, the second reading and known concentrations of the target analyte.

5. The fluid analyzer of claim 1, wherein the target analyte is a metabolite.

6. The fluid analyzer of claim 1, wherein the second reading is correlated to a zero analyte concentration level.

7. The fluid analyzer of claim 1, wherein the fluid sample is a biological sample, and wherein the measurement of the target analyte concentration is configured into a form suitable for a medical diagnostic purpose.

8. The fluid analyzer of claim 1, wherein the fluid sample is a non-biological sample.

9. The fluid analyzer of claim 1, wherein controlling the potentiostat to apply the first voltage potential occurs prior to controlling the potentiostat to apply the second voltage potential.

10. The fluid analyzer of claim 1, wherein controlling the potentiostat to apply the second voltage potential occurs prior to controlling the potentiostat to apply the first voltage potential.

11. The fluid analyzer of claim 1, wherein the second reading is indicative of non-faradaic current.

* * * * *